US012747458B2

(12) United States Patent
Song et al.

(10) Patent No.: US 12,747,458 B2
(45) Date of Patent: Sep. 29, 2026

(54) METHOD OF REDUCING NITROGEN OXIDE CONCENTRATION IN SAMPLE, BIOREACTOR, AND PLUG FLOW REACTOR

(71) Applicants: Samsung Electronics Co., Ltd., Suwon-si (KR); Korea Advanced Institute of Science and Technology, Daejeon (KR)

(72) Inventors: Seung Hoon Song, Suwon-si (KR); Heejoo Han, Daejeon (KR); Woo Yong Shim, Suwon-si (KR); Sukhwan Yoon, Daejeon (KR); Jae-Young Kim, Suwon-si (KR); Sojung Yoon, Daejeon (KR); Yu Kyung Jung, Suwon-si (KR)

(73) Assignees: SAMSUNG ELECTRONICS CO., LTD., Gyeonggi-Do (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 385 days.

(21) Appl. No.: 18/471,509

(22) Filed: Sep. 21, 2023

(65) Prior Publication Data

US 2024/0102054 A1 Mar. 28, 2024

(30) Foreign Application Priority Data

Sep. 22, 2022 (KR) ........................ 10-2022-0120102

(51) Int. Cl.

| | |
|---|---|
| ***C12N 1/20*** | (2026.01) |
| ***C01B 21/00*** | (2006.01) |
| ***C02F 3/28*** | (2023.01) |
| ***C02F 3/34*** | (2023.01) |
| ***C12M 1/00*** | (2006.01) |
| ***C12N 15/52*** | (2006.01) |
| ***C12P 3/00*** | (2006.01) |
| ***C12R 1/00*** | (2006.01) |
| *C02F 101/16* | (2006.01) |

(52) U.S. Cl.

CPC .............. *C12P 3/00* (2013.01); *C02F 3/2813* (2013.01); *C02F 3/286* (2013.01); *C02F 3/341* (2013.01); *C02F 3/342* (2013.01); *C02F 3/346* (2013.01); *C12M 29/04* (2013.01); *C12M 29/18* (2013.01); *C12M 29/20* (2013.01); *C02F 2101/16* (2013.01)

(58) Field of Classification Search

CPC .......... C12N 1/20; C12N 15/52; C12R 1/185; C01B 21/00; C02F 3/283

See application file for complete search history.

(56) References Cited

U.S. PATENT DOCUMENTS

| | | | | |
|---|---|---|---|---|
| 5,891,408 | A | 4/1999 | Buisman et al. | |
| 7,998,445 | B2 | 8/2011 | Jurng et al. | |
| 12,024,710 | B2 * | 7/2024 | Shim | B01D 53/84 |
| 12,534,392 | B2 * | 1/2026 | Smith | C02F 3/305 |
| 2003/0026744 | A1 | 2/2003 | Hakka et al. | |
| 2022/0177896 | A1 | 6/2022 | Shim et al. | |
| 2024/0018026 | A1 * | 1/2024 | Smith | C02F 3/105 |

FOREIGN PATENT DOCUMENTS

| | | | |
|---|---|---|---|
| CN | 110526528 | A | 12/2019 |
| KR | 100407204 | B1 | 5/2004 |
| KR | 20100104173 | A | 9/2010 |
| KR | 101094672 | B1 | 12/2011 |
| KR | 20220079390 | A | 6/2022 |
| WO | 9624434 | A1 | 8/1996 |

OTHER PUBLICATIONS

B. Chandrashekhar et al., "Treatment of ferrous-NTA-based NOx scrubber solution by an up-flow anaerobic packed bed bioreactor", Applied Microbiology and Biotechnology, 2015, 99(12), 5281-5293.

Peter van der Maas et al., "NO Removal in Continuous BioDeNOx Reactors: Fe(II)EDTA2 Regeneration, Biomass Growth, and EDTA Degradation", Biotechnology and Bioengineering, 2006, pp. 575-584, vol. 94.

Peter van der Maas et al., "NO Removal in Continuous BioDeNOx Reactors: Fe(II)EDTA2-Regeneration, Biomass Growth, and EDTA Degradation", Biotechnology and Bioengineering, Apr. 4, 2006, pp. 575-584, vol. 94, No. 3.

(Continued)

*Primary Examiner* — Maryam Monshipouri

(74) *Attorney, Agent, or Firm* — CANTOR COLBURN LLP

(57) ABSTRACT

A method of reducing a concentration of a nitrogen oxide, the method comprising: contacting a microorganism with a nitrogen oxide-containing sample to reduce the concentration of the nitrogen oxide in the sample, wherein the contacting comprises contacting the microorganism with Fe(II)(L)-$NO_x$ in a bioreactor, wherein the Fe(II)(L)-$NO_x$ is a complex in which a chelating agent, $Fe^{2+}$, and $NO_x$ are chelated, wherein L is the chelating agent, and wherein $NO_x$ is a nitrogen oxide ligand.

15 Claims, 4 Drawing Sheets

(56) References Cited

OTHER PUBLICATIONS

Yanling Wang et al., "Evaluation of NOx removal from flue gas and Fe(II)EDTA regeneration using a novel BTF-ABR integrated system", Journal of Hazardous Materials, Mar. 25, 2021, pp. 1-10, vol. 415.
Yi Wang et al., "Improved modelling of soil NOx emissions in a high temperature agricultural region: role of background emissions on NO2 trend over the US", Environ. Res. Lett., 2021, pp. 1-9, vol. 16, No. 084061.
Yong Beom Jo et al., "NH3 selective catalytic reduction (SCR) of nitrogen oxides (NOx) over activated sewage sludge char", Korean J. Chem. Eng., 2010, pp. 106-113, vol. 28, No. 1.
Zuoming Zhou et al., "Enhanced NOx removal from flue gas by an integrated process of chemical absorption coupled with two-stage biological reduction using immobilized microorganisms", Process Safety and Environmental Protection 91, 325-332 (2013).

* cited by examiner

METHOD OF REDUCING NITROGEN OXIDE CONCENTRATION IN SAMPLE, BIOREACTOR, AND PLUG FLOW REACTOR

CROSS-REFERENCE TO RELATED APPLICATION

This application claims the benefit of and priority to Korean Patent Application No. 10-2022-0120102, filed on Sep. 22, 2022, in the Korean Intellectual Property Office, and all the benefits accruing therefrom under 35 U.S.C. § 119, the entire content of which is incorporated by reference herein.

BACKGROUND

1. Field

The present disclosure relates to a method of reducing a concentration of a nitrogen oxide in a sample and a plug flow reactor using the same.

2. Description of the Related Art

Nitrogen oxides ($NO_x$) are a class of air pollutants mainly emitted during the combustion process of fuels, and includes nitrous oxide ($N_2O$), nitric oxide (NO), dinitrogen trioxide ($N_2O_3$), nitrogen dioxide ($NO_2$), dinitrogen tetroxide ($N_2O_4$), and dinitrogen pentoxide ($N_2O_5$), among which NO and $NO_2$ are the main causes of air pollution. $N_2O$, along with carbon dioxide ($CO_2$), methane ($CH_4$), and chlorofluorocarbons (CFCs), absorb and store heat in the atmosphere, thereby causing a greenhouse effect. $N_2O$ is one of the six greenhouse gases subject to regulation by the Kyoto Protocol, and has a global warming potential (GWP) of 310, which means that it has a higher warming effect per unit mass than $CO_2$ (GWP of 1) and $CH_4$ (GWP of 21). In addition, nitrogen oxides are a cause of smog and acid rain, and through chemical reactions in the air, can form secondary ultrafine particles and dust, and increase the concentration of ground-level ozone, which adversely affect respiratory health.

In nitrogen oxide removal processes, technologies such as selective catalytic reduction (SCR), selective non-catalytic reduction (SNCR), and/or and scrubbing and adsorption, which are chemical reduction methods, are applied. These chemical methods have issues such as costs of energy and the catalysts required for the process, and treatment of secondary wastes generated therefrom. In addition, in the case of SCR or SNCR, another greenhouse gas, $N_2O$, may be generated as a result of incomplete reduction in the process of reducing NO and $N_2O$. Unlike the chemical technologies having such issues, biological processes are environmentally friendlier with advantages such as a relatively simpler principles, no use of extreme conditions such as high temperature and high pressure, and lower generation of secondary wastes or wastewater. In a biological process, microorganisms acting as a biological catalyst may be used instead of a chemical catalyst, to oxidize or reduce $NO_x$, or to fix $NO_x$ as part of a cell.

However, there remains a continuing need for efficiently removing nitrogen oxides from a sample and a bioreactor using a microorganism.

SUMMARY

Provided is a method of reducing a concentration of a nitrogen oxide concentration in a nitrogen oxide-containing sample, the method including contacting a microorganism with a nitrogen oxide-containing sample to reduce the concentration of the nitrogen oxide concentration in the sample, wherein the contacting includes contacting the microorganism with Fe(II)(L)-$NO_x$ in a bioreactor, wherein the Fe(II)(L)-$NO_x$ is a complex in which a chelating agent, $Fe^{2+}$, and $NO_x$ are chelated, wherein L is the chelating agent, and wherein $NO_x$ is a nitrogen oxide ligand.

In one or more embodiments, L may be ethylenediamine, diethylenetriamine, triethylenetetraamine, hexamethylenetetramine, N-(2-hydroxyethyl)ethylenediaminetriacetic acid, ethylenediaminetetraacetic acid, iminodiacetic acid, nitrilotriacetic acid, diethylenetriaminepentaacetic acid, or a combination thereof Additional aspects will be set forth in part in the detailed description that follows and, in part, will be apparent from the detailed description, or may be learned by practice of the presented exemplary embodiments herein.

According to an aspect, provided is a plug flow reactor for reducing a concentration of a nitrogen oxide in a sample, the plug flow reactor including two or more compartments separated by a porous plate, wherein the porous plate comprises a plurality of pores, and a plurality of carriers to which a microorganism is adsorbed, wherein the plurality of carriers are disposed in each of the two or more compartments.

In the plug flow reactor, the porous plates may have a plurality of pores. The pores may have an average diameter through which a carrier may not pass but a fluid may pass. The carrier may be one to which microorganisms may be attached, and one that does not inhibit growth of the microorganisms. The carrier may be made of a plastic material such as high-density polyethylene (HDPE), polypropylene, or the like, or a combination thereof. The carrier may have various shapes. The carrier may have a density of about 0.9 grams per cubic centimeter (g/cm$^3$) to about 0.97 g/cm$^3$. The carrier may have a specific surface area of about 600 square meters per cubic meter (m$^2$/m$^3$) or greater. The carrier may be capable of acting as a carrier at about 5° C. to about 60° C.

For example, the carrier may be a micro-disc in which pores are formed. A diameter of the carrier may be about 0.5 centimeters (cm) to about 1.2 cm, about 0.6 cm to about 1.2 cm, about 0.7 cm to about 1.2 cm, about 0.8 cm to about 1.2 cm, about 0.6 cm to about 1.1 cm, about 0.7 cm to about 1.1 cm, about 0.7 cm to about 1.0 cm, about 0.7 cm to about 0.9 cm, or about 0.8 cm to about 0.9 cm.

In the plug flow reactor, the plurality of carriers may be disposed in each compartment at a ratio of about 0 volume percent (vol %) to about 90 vol %, based on a total volume of each compartment.

In the compartments, an interface where a first compartment and a second compartment are in contact with each other may include the porous plate, and a surface where an inlet or an outlet is formed may include a material that is impermeable to the plurality of carriers and the fluids. Therefore, when the interface where a first compartment and a second compartment are in contact with each other includes the porous plate, a fluid introduced through an inlet flows into each compartment through the porous plate, and due to the porous plate, only the fluid passes through the porous plate while the carriers do not pass, and thus, bacterial compositions in the fluid present in each compartment or space before passing through the porous plate may be differentiated from those in each compartment or space after passing through the porous plate. In addition, the bacterial compositions in the fluid present in each compartment or space before passing through the porous plate and in each compartment or space after passing through the porous plate may be differentiated according to residence time in each compartment. The growth of each bacterium may vary depending on the conditions in each compartment, for example, oxygen concentration, pH, temperature, type of nutrients, or the like, or a combination thereof. The compartments may be independently maintained under anaerobic conditions or microaerobic conditions.

In the plug flow reactor, when the two compartments are regarded as a lower compartment and an upper compartment, respectively, and a portion where the influent is introduced is regarded as the lowest end, the dissolved oxygen concentration may be about 0.8 vol % to about 1.1 vol % at the lowest end, about 0.3 vol % to about 0.5 vol % in the lower compartment, and about 0 vol % in the upper compartment, based on total volume of the compartment. When the size of compartments increases according to an increase in the bioreactor size, the oxygen concentration of the first influent may be reduced to about 1 vol %, and the oxygen concentration in the next compartment may be reduced to about 0.5 vol % or less, each based on total volume of the compartment.

There may be two or more compartments, or a plurality of compartments. In some embodiments, there may be, for example, 2, 3, 4, 5, 6, 7, 8, 9, or 10 compartments.

The compartments may include denitrifying microorganisms, iron reducing microorganisms, or a combination thereof. The compartments may include a buffer portion in which growth of facultative anaerobes, which respire and grow at low $O_2$ concentrations, predominates.

The compartments may include a first compartment including a bacterium that reduces $NO_2$ and/or NO to $N_2$, and a second compartment including a bacterium that reduces Fe(III) to Fe(II).

In addition, the sample may flow in the direction from the first compartment (including a bacterium that reduces $NO_2$ and/or NO to $N_2$) to the second compartment (including a bacterium that reduces Fe(III) to Fe(II)).

In the bioreactor and the plug flow reactor, the bacterium that reduces $NO_2$ and/or NO to $N_2$ may be a microorganism of the family Rhodocyclaceae, Zoogloeaceae, Rhodobacteraceae, Clostridiaceae, or a combination thereof. The bacterium belonging to the genus Rhodocyclaceae may be a microorganism of the genus *Dechloromonas*. The bacterium belonging to the family Rhodobacteraceae may be a microorganism of the genus *Paracoccus*. The bacterium belonging to the family Clostridiaceae may be a microorganism of the genus *Clostridium*.

The bacterium that reduces Fe(III) to Fe(II) may be a microorganism of the family Clostridiaceae, Shewanellaceae, Geobacteraceae, Rhodobacteraceae, Pseudomonadaceae, or a combination thereof. In addition, the bacterium that reduces Fe(III) to Fe(II) may be a microorganism of the genus *Pseudomonas*. The bacterium belonging to the family Clostridiaceae may be a microorganism of the genus *Clostridium*.

The bacterium belonging to the family Shewanellaceae may be a microorganism of the genus *Shewanella*. The bacterium belonging to the family Geobacteraceae may be a microorganism of the genus *Geobacter*. The bacterium belonging to the family Rhodobacteraceae may be a microorganism of the genus *Paracoccus*.

The nitrogen oxide ($NO_x$) may include NO, $N_2O$, $NO_2$, $N_2O_3$, $N_2O_4$, $N_2O_5$, salts thereof, chelated forms thereof, dissolved forms thereof, or a combination thereof. The chelated form may be, for example, in the form of Fe(II)(L)-$NO_x$, where the $NO_x$ moiety is a ligand to the Fe(II) center. It is to be understood that "Fe(II)(L)-$NO_x$" represents that a chelating agent L, $Fe^{2+}$, and $NO_x$ are chelated to each other to form a complex. The chelating ligand L may be, for example, ethylenediamine, diethylenetriamine, triethylenetetramine, hexamethylenetetramine, N-(2-hydroxyethyl)ethylenediaminetriacetic acid (HEDTA), ethylenediaminetetraacetic acid (EDTA), iminodiacetic acid, nitrilotriacetic acid (NTA), diethylenetriaminepentaacetic acid (DTPA), or a combination thereof, but embodiments are not limited thereto. Accordingly, Fe(II)(L)-$NO_x$ may be in a form in which the nitrogen oxide such as NO, $N_2O$, $NO_2$, $N_2O_3$, $N_2O_4$, $N_2O_5$ is modified to become soluble in an aqueous solution. Fe(II)(L)-$NO_x$ may be formed by contacting an aqueous solution including the Fe(II)(L) with the nitrogen oxide species. The contacting may be, for example, by mixing the aqueous medium with liquid nitrogen oxide species or contacting the aqueous medium with a gaseous nitrogen oxide species. However, embodiments are not limited thereto, and interpretations should not be limited to this specific mechanism, with respect to the reduction of nitrogen oxide concentration by the microorganisms. In one or more embodiments embodiment, the nitrogen oxide may be nitric oxide (NO).

The plug flow reactor may include an inlet through which a nitrogen oxide-containing sample is introduced into the plug flow reactor. The inlet may be connected (for example, directly connected) to a nitrogen oxide source. In addition, the inlet may be fluidly connected to a vessel or a reactor generating or containing nitrogen oxide, for example, Fe(II)(L)-$NO_x$. In one or more embodiments, the inlet may be fluidly connected to a vessel generating Fe(II)(L)-$NO_x$ or a vessel including Fe(II)(L)-$NO_x$.

In one or more embodiments, Fe(II)(L)-$NO_x$ may be Fe(II)(EDTA)-NO.

The plug flow reactor may include an outlet through which a reacted nitrogen oxide-containing sample is discharged. The outlet may be fluidly connected to the inlet so that the discharged sample may be recirculated to the plug flow reactor through the inlet. The outlet and the inlet may be fluidly connected through a vessel or reactor generating or containing the nitrogen oxide, for example, Fe(II)(L)-$NO_x$.

The plug flow reactor may further include a vessel or a reactor generating or containing nitrogen oxide, for example, Fe(II)(L)-$NO_x$, fluidly connected to the inlet. The vessel or reactor generating or including Fe(II)(L)-$NO_x$ may include an inlet through which a nitrogen oxide-containing sample may be introduced. In one or more embodiments, the vessel generating Fe(II)(L)-$NO_x$ or the vessel comprising Fe(II)(L)-$NO_x$ each includes an inlet through which the nitrogen oxide-containing sample may be introduced.

The vessel or the reactor generating Fe(II)(L)-$NO_x$ or including Fe(II)(L)-$NO_x$ may include a gas outlet capable of discharging the nitrogen oxide reacted in the plug flow reactor, for example, a reduced nitrogen oxide gas such as $N_2O$ and/or $N_2$. Accordingly, the nitrogen oxide that is reduced in the plug flow reactor may be discharged through the gas outlet. The vessel or the reactor generating Fe(II)(L)-$NO_x$ or including Fe(II)(L)-$NO_x$ may include an inlet through which the reacted fluid discharged from the outlet of the plug flow reactor is introduced.

The vessel or the reactor generating Fe(II)(L)-$NO_x$ or including Fe(II)(L)-$NO_x$ may include a fluid level regulator for regulating the fluid level. The fluid level regulator may open or close the fluid outlet when the fluid level reaches a specified level. Accordingly, the reduction reaction of the nitrogen oxide species in the plug flow reactor may be performed together with continuous flow of the fluid.

The plug flow reactor may be fluidly connected to a vessel containing organic matter and/or a vessel including Fe(III)(L). The organic matter-containing container may include wastewater including organic matter. The wastewater may include microorganisms. In some embodiments, the plug flow reactor may be not connected to an electron donor, nutrients, and/or a vessel containing an electron donor and nutrients, other than the wastewater. The electron donor may be, for example, ethanol, but embodiments are not limited thereto. The nutrients may be, for example, a chemically defined medium. The Fe(III)(L) may be, for example, Fe(III)(EDTA). The microorganism may be single microorganism or a combination of two or more different microorganisms. The combination of microorganisms may be a defined combination of microorganisms obtained by mixing two or more isolated single microorganisms. In addition, the combination of microorganisms may be a naturally or artificially formed microbial collection. The mixture may be, for example, wastewater or an activated sludge including a microbial collection. The wastewater may be wastewater from an industrial plant, or wastewater from a residential space, for example, a domestic sewage plant. For example, the activated sludge may be derived from a wastewater treatment facility.

The microorganisms may be recombinant microorganisms of the genus *Escherichia* that are capable of reducing nitrogen oxides, including a nitrous oxide reductase gene, which encodes an enzyme that catalyzes the reaction of converting $N_2O$ to $N_2$ with $N_2O$ as a substrate. Examples of recombinant microorganisms of the genus *Escherichia* include those disclosed in US Patent Publication No. US2022/0177896A1, the entire content of which is incorporated herein.

The recombinant microorganism of the genus *Escherichia* may include a genetic modification that increases expression of a nosZ gene encoding a nitrous oxide reductase NosZ in the recombinant microorganism, a nosR gene encoding NosR, a nosD gene encoding NosD, a nosF gene encoding NosF, a nosY gene encoding NosY, and an apbE gene encoding ApbE, wherein the nosZ gene, the nosR gene, the nosD gene, the nosF gene, the nosY gene, and the apbE gene are derived from a microorganism of the genus *Pseudomonas*, the genus *Paracoccus*, or a combination thereof.

In some embodiments, the genetic modification may be a genetic modification that increases the copy number of the nosZ gene, the copy number of the nosR gene, the copy number of the nosD gene, the copy number of the nosF gene, the copy number of the nosY gene, and the copy number of the apbE gene. The genetic modification may include the introduction of the nosZ, nosR, nosD, nosF, nosY, and apbE genes, for example, via a vehicle such as a vector. The gene(s) may or may not be inserted within a chromosome (genome) of the recombinant microorganism. The introduced genes may include a plurality of copies of the genes, for example, a copy number of the genes may be, independently, 2 or greater, 5 or greater, 10 or greater, 25 or greater, 50 or greater, 100 or greater, or 1000 or greater.

The nitrous oxide reductase is an enzyme that catalyzes a conversion of $N_2O$ to $N_2$, by using $N_2O$ as a substrate. The NosZ is a protein encoded by the nosZ gene and is an enzyme that catalyzes the conversion of $N_2O$ to $N_2$, that is, a nitrous oxide reductase. The NosZ protein may be a 130 kilodalton (kDa) homodimeric metalloprotein including two copper centers in each monomer, namely, $CU_A$ and $Cu_Z$.

The NosR is a polytopic membrane protein encoded by the nosR gene and serves as an electron donor for $N_2O$ reduction. The NosD is encoded by the nosD gene and may be essential for the formation of the [4Cu:2S] copper site CuZ in the NosZ protein. The NosD may supply sulfur (S) to the NosZ. The NosF and the NosY are encoded by the nosF gene and the nosY gene, respectively, and the NosF and the NosY may together form a complex, for example, a tetramer, that serves as an ABC transporter. The ApbE is a protein encoded by the apbE gene and is a flavinyltransferase that transfers flavin to the NosR.

The microorganisms of the genus *Pseudomonas* may be *Pseudomonas stutzeri, Pseudomonas aeruginosa*, or a combination thereof.

The microorganisms of the genus *Paracoccus* may be *Paracoccus versutus.*

The microorganisms may be of the genus *Escherichia*, for example, *Escherichia coli.*

The microorganisms capable of reducing $NO_x$ and Fe(III) may be *Pseudomonas, Paracoccus, Shewanella, Thiobacillus, Clostridium*, or a combination thereof.

The microbial source or vessel containing microorganisms or Fe(III)(L) source or vessel including Fe(III)(L) may be fluidly connected to the plug flow reactor through the inlet, or through another part. The microbial source or vessel containing microorganisms or Fe(III)(L) source or vessel including Fe(III)(L) may be fluidly connected to the plug flow reactor, together or individually.

In the plug flow reactor, a ratio of the height to the diameter of the reactor may be about 1:10 or greater, for example, about 1:10 to about 1:50, about 1:10 to about 1:100, about 1:10 to about 1:1,000, or about 1:10 to about 1:10,000. The height or length of the plug flow reactor may be sufficient to reduce nitrogen oxides in the fluid flowing into the inlet. In the plug flow reactor or system, the residence time of the microorganisms may be a time sufficient to reduce nitrogen oxides in the fluid flowing through the inlet. The residence time may vary depending on the length and/or diameter of the plug flow reactor, the ratio of the length to the diameter, type and concentration of the microorganisms, concentration of nitrogen oxides introduced, and/or the flow rate. The temperature in the plug flow reactor may be room temperature, for example, about 4° C. to about 40° C., about 10° C. to about 40° C., about 15° C. to about 35° C., about 20° C. to about 30° C., about 22° C. to about 27° C., or about 25° C. The pH in the plug flow reactor may be about 6.5 to about 7.5, for example, about 7.0 to about 7.4, about 7.1 to about 7.3, or about 7.2.

FIG. 1 is a diagram showing an example of a plug flow reactor system according to one or more embodiments. An example of the plug flow reactor system will be described with reference to FIG. 1 as follows. The plug flow reactor 900' has two compartments 940 and 950 separated by three porous plates 910, 920, and 930, and buffer spaces 960 and 970 that are each separated by the porous plates 910 and 930 and a wall made of a material impermeable to fluids. The compartments 940 and 950 may include a plurality of carriers to which each of the microorganisms are attached. The plug flow reactor 900' may include an inlet 900 through which a fluid is introduced and an outlet 980 through which the fluid is discharged. The discharged fluid may be a fluid in which biological reduction reactions of nitrogen oxide are performed when the introduced fluid is incubated in each compartment including the microorganisms. The plug flow reactor 900' may include a compartment 960 including a buffer space between the inlet 900 and the first compartment 910. The plug flow reactor 900' may also include a compartment 970, including a buffer space between the last compartment 950, in which the fluid resides, and the outlet 980. The outlet 980 may be directly fluidly connected to the inlet 900 in a fluid flow direction, or may be indirectly fluidly connected to the inlet 900. For example, the outlet 980 may be fluidly connected to the inlet 900 through a vessel 200 generating or containing nitrogen Fe(II)(EDTA)-NO. In FIGS. 1, 800 and 500 indicate fluidly connecting passages. The compartments 940, 950, 960, and 970 may each include a sampling port 912, or 912'.

The plug flow reactor 900' may be fluidly connected to the vessel 200 generating Fe(II)(L)-$NO_x$ or including Fe(II)(L)-$NO_x$. The vessel 200 generating Fe(II)(L)-$NO_x$ or including Fe(II)(L)-$NO_x$ may include an inlet 210 fluidly connected to the nitrogen oxide source 100. The nitrogen oxide may be supplied to the vessel by purging. The vessel 200 generating Fe(II)(L)-$NO_x$ or including Fe(II)(L)-$NO_x$ may include an outlet 400 for discharging the reduced nitrogen oxide. The outlet may include a suction device 410 for sucking the reduced nitrogen oxide gas. The suction device 410 may be a hood. The vessel 200 generating Fe(II)(L)-$NO_x$ or including Fe(II)(L)-$NO_x$ may include a fluid level regulator 300. The fluid level regulator 300 may open and close the fluid outlet so that the fluid flows out when a fluid level reaches a predetermined value. The vessel 200 generating Fe(II)(L)-$NO_x$ or including Fe(II)(L)-$NO_x$ may be fluidly connected to a vessel or a reactor 310 containing the fluid discharged by the fluid level regulator 300. An example of L may be EDTA.

The plug flow reactor 900' may be fluidly connected to an organic matter source or organic matter-containing vessel 600, or an Fe(III)(L) source or Fe(III)(L)-containing vessel 610. The plug flow reactor 900' may be fluidly connected to the organic matter source or organic matter-containing vessel 600 and the Fe(III)(L) source or Fe(III)(L)-containing vessel 610 through a combining fluidly connected passage. In addition, the plug flow reactor 900' may be fluidly connected to the organic matter source or the organic matter-containing vessel 600, or the Fe(III)(L) source or the Fe(III)(L)-containing vessel 610 separately. The plug flow reactor 900' may be fluidly connected to any one of the organic matter source or organic matter-containing vessel 600, the Fe(III)(L) source or Fe(III)(L)-containing vessel 610, and the compartments (940, 950, 960, 970). The plug flow reactor 900' may include a means for transporting fluid between portions thereof that are fluidly connected, for example, a pump such as a peristaltic pump. The plug flow reactor 900' may also include a port 700 (not shown) for sampling oxygen samples.

The Fe(III)(L) may be, for example, Fe(III)(EDTA). The microorganism may be a single microorganism or a combination of two or more different microorganisms. The combination of microorganisms may be a defined combination of microorganisms obtained by mixing two or more isolated single microorganisms. In addition, the combination of microorganisms may be a naturally or artificially formed microbial collection. The mixture may be, for example, a wastewater or an activated sludge including a microbial collection. The wastewater may be a wastewater from an industrial plant or a wastewater from a residential space, for example, a domestic sewage system. The activated sludge may be derived from a wastewater treatment facility.

According to another aspect, a method of reducing a concentration of nitrogen oxide includes contacting a microorganism with a nitrogen oxide-containing sample to reduce the concentration of the nitrogen oxide in the sample, wherein the contacting includes contacting the microorganism with Fe(II)(L)-NO in a bioreactor, wherein the Fe(II)(L)-$NO_x$ is a complex in which a chelating agent, $Fe^{2+}$, and $NO_x$ are chelated, wherein L is the chelating agent, and wherein $NO_x$ is a nitrogen oxide ligand.

In the method, the contacting may include continuously introducing a Fe(II)(L)-NO into a bioreactor including the microorganism. The contacting may include continuously introducing an Fe(II)(L)-NO into the bioreactor including the microorganism, and reacting in a batchwise manner without continuous introduction.

In the method, unless otherwise mentioned, the microorganism, nitrogen oxide and nitrogen oxide-containing samples, and Fe(II)-(L)-NO are as described in the plug flow reactor for use in reducing nitrogen oxide concentration.

The bioreactor may be any known bioreactor. The bioreactor may be, for example, a plug flow reactor for reducing nitrogen oxide concentration in a sample, including two or more compartments separated by porous plates, and a plurality of carriers to which microorganisms are adsorbed, disposed in each of the compartments. The plug flow reactor is as described above.

The method may include introducing a sample including a nitrogen oxide through an inlet of the bioreactor. In addition, the method may include preparing Fe(II)(L)-NO by contacting a nitrogen oxide with an aqueous solution including Fe(II)(L), before the introducing process into the bioreactor. The nitrogen oxide may be any material including nitrogen oxide, as defined herein. For example, the nitrogen oxide may be in a form of an exhaust gas or wastewater containing the nitrogen oxide. The introducing may be introducing directly through the inlet from the nitrogen oxide source, or may be introducing from the vessel or reactor generating Fe(II)(L)-$NO_x$ or including Fe(II)(L)-$NO_x$.

The method may include adjusting the fluid level by opening and closing a fluid outlet when a predetermined level of fluid level is reached in the vessel or the bioreactor generating Fe(II)(L)-$NO_x$ or including Fe(II)(L)-$NO_x$.

The method may include recirculating the reacted fluid being discharged from the bioreactor to the inlet of the reactor. The recirculating may include recirculating through the vessel or bioreactor generating Fe(II)(L)-$NO_x$ or including Fe(II)(L)-$NO_x$.

The method may further include introducing the microorganism into the bioreactor to replenish an amount of the microorganism. The method may include introducing the organic matter into the bioreactor to replenish an amount of the organic matter. The organic matter may include nutrients for growth of the microorganism, such as a carbon source and/or metal ions. The organic matter may include microorganisms, for example, a microbial collection, along with the organic matter, such as wastewater. Also, the method may include introducing Fe(III)(L) into the bioreactor to replenish an amount of Fe(III)(L) that is depleted. The introducing of the microorganisms or organic matter into the bioreactor may be introducing the fluid containing organic matter from an organic matter source or an organic matter-containing vessel. The introducing of Fe(III)(L) into the bioreactor may be introducing a fluid including Fe(III)(L) from a Fe(III)(L) source or a Fe(III)(L)-containing vessel into the bioreactor. The introducing into the bioreactor may be introducing into any one of the compartments 940, 950, 960, and/or 970 of the plug flow reactor.

In the method, the Fe(III)(L) may be, for example, Fe(III)(EDTA). The microorganism may be a single microorganism or a combination of two or more different microorganisms. The combination of microorganisms may be a defined combination of microorganisms obtained by mixing two or more isolated single microorganisms. In addition, the combination of microorganisms may be a naturally or artificially formed microbial collection. The mixture may be, for example, a wastewater or an activated sludge including a microbial collection. The wastewater may be a wastewater from an industrial plant or a wastewater from a residential space, for example, a domestic sewage system. The activated sludge may be derived from a wastewater treatment facility.

The microorganism may be a recombinant microorganism of the genus *Escherichia* that is capable of reducing nitrogen oxides, including a nitrous oxide reductase gene, which encodes an enzyme that catalyzes the reaction of converting $N_2O$ to $N_2$, with $N_2O$ as a substrate. Examples of recombinant microorganisms of the genus *Escherichia* are disclosed in US Patent Publication No. US2022/0177896A1, the content of which are incorporated herein in their entirety.

The recombinant microorganism of the genus *Escherichia* may include a genetic modification that increases expression of a nosZ gene encoding a nitrous oxide reductase NosZ in the recombinant microorganism, a nosR gene encoding NosR, a nosD gene encoding NosD, a nosF gene encoding NosF, a nosY gene encoding NosY, and an apbE gene encoding ApbE, wherein the nosZ gene, the nosR gene, the nosD gene, the nosF gene, the nosY gene, and the apbE gene are derived from a microorganism of the genus *Pseudomonas*, the genus *Paracoccus*, or a combination thereof.

In some embodiments, the genetic modification may be a genetic modification that increases the copy number of the nosZ gene, the copy number of the nosR gene, the copy number of the nosD gene, the copy number of the nosF gene, the copy number of the nosY gene, and the copy number of the apbE gene. The genetic modification may include the introduction of the nosZ, nosR, nosD, nosF, nosY, and apbE genes, for example, via a vehicle such as a vector. The gene(s) may or may not be inserted within a chromosome (genome) of the recombinant microorganism. The introduced genes may include a plurality of copies of the genes, for example, a copy number of the genes may be, independently, 2 or greater, 5 or greater, 10 or greater, 25 or greater, 50 or greater, 100 or greater, or 1000 or greater.

The nitrous oxide reductase is an enzyme that catalyzes a conversion of $N_2O$ to $N_2$, by using $N_2O$ as a substrate. The NosZ is a protein encoded by the nosZ gene and is an enzyme that catalyzes the conversion of $N_2O$ to $N_2$, that is, a nitrous oxide reductase. The NosZ protein may be a 130 kilodalton (kDa) homodimeric metalloprotein including two copper centers in each monomer, namely, $CU_A$ and $Cu_z$.

The NosR is a polytopic membrane protein encoded by the nosR gene and serves as an electron donor for $N_2O$ reduction. The NosD is encoded by the nosD gene and may be essential for the formation of the [4Cu:2S] copper site CuZ in the NosZ protein. The NosD may supply sulfur (S) to the NosZ. The NosF and the NosY are encoded by the nosF gene and the nosY gene, respectively, and the NosF and the NosY may together form a complex, for example, a tetramer, that serves as an ABC transporter. The ApbE is a protein encoded by the apbE gene and is a flavinyltransferase that transfers flavin to the NosR.

The microorganisms of the genus *Pseudomonas* may be *Pseudomonas stutzeri, Pseudomonas aeruginosa*, or a combination thereof.

The microorganisms of the genus *Paracoccus* may be *Paracoccus versutus.*

The microorganisms may be of the genus *Escherichia*, for example, *Escherichia coli.*

The microorganisms capable of reducing $NO_x$ and Fe(III) may be *Pseudomonas, Paracoccus, Shewanella, Thiobacillus, Clostridium*, or a combination thereof.

In the method, the microorganisms may be adsorbed to the carrier. The microorganisms may be a microbial collection included in wastewater such as domestic sewage.

In the method, the bioreactor may be the plug flow reactor, and may introduce the fluid sample through the inlet. In the plug flow reactor, there may be 2, 3, 4, 5, 6, 7, 8, 9, or 10 compartments. For example, the bioreactor may include two or four compartments for microbial reactions. In addition, the compartments may include buffer compartments at the inlet and/or the outlet.

In the method, the inflowing fluid may be incubated for a predetermined residence time in each compartment so that denitrification reactions and iron reduction reactions may occur by the microorganism(s).

In the method, the compartments may include a buffer portion in which growth of facultative anaerobes, which respire and grow at low $O_2$ concentrations, predominates. The compartments may include a first compartment including a bacterium that reduces $NO_2$ and/or NO to $N_2$, and a second compartment that includes a bacterium that reduces Fe(III) to Fe(II). In addition, the sample may flow from the first compartment to the second compartment in the bioreactor.

In the method, the bacterium that reduces $NO_2$ and/or NO to $N_2$ may be a microorganism of the family Rhodocyclaceae, Zoogloeaceae, Rhodobacteraceae, Clostridiaceae, or a combination thereof. The bacterium belonging to the family Rhodocyclaceae may be a microorganism of the genus *Dechloromonas*. The bacterium belonging to the family Rhodobacteraceae may be a microorganism of the genus *Paracoccus*. The bacterium belonging to the family Clostridiaceae may be a microorganism of the genus *Clostridium.*

In the method, the bacterium that reduces Fe(III) to Fe(II) may a microorganism of the family Clostridiaceae, Shewanellaceae, Geobacteraceae, Rhodobacteraceae, or a combination thereof. In addition, the bacterium that reduce Fe(III) to Fe(II) may belong to the genus *Pseudomonas*. The bacterium belonging to the family Clostridiaceae may be *Clostridium*. The bacterium belonging to the family Shewanellaceae may be a microorganism of the genus *Shewanella*. The bacterium belonging to the family Geobacteraceae may be a microorganism of the genus *Geobacter*. The bacterium belonging to the family Rhodobacteraceae may be a microorganism of the genus *Paracoccus.*

In the method, the contacting may include flowing a nitrogen oxide-containing sample through a bioreactor including the microorganism. In the method, the nitrogen oxide-containing sample may be Fe(II)(EDTA)-NO. In the method, the sample flowing out from the bioreactor may be recirculated to the bioreactor. The sample flowing out of the bioreactor may be recirculated to the bioreactor by being combined with the nitrogen oxide-containing sample. The bioreactor may be capable of introducing wastewater or Fe(III)(EDTA) solution by being fluidly connected to a wastewater-containing vessel or a Fe(III)(EDTA)-containing vessel. The method may further include introducing wastewater or Fe(III)(EDTA) into the bioreactor. The wastewater may be used for providing assimilable organic matter for the microorganisms in the bioreactor. Accordingly, the Fe(III)(EDTA) solution is for providing assimilable organic matter for the microorganisms in addition to the wastewater, and may be used as an alternative to the wastewater. The wastewater may be, for example, factory wastewater or domestic sewage from living spaces. Since wastewater is not a chemically defined medium, wastewater may be advantageous to the process as is relatively inexpensive to prepare or supply.

In the method, the plug flow reactor may not be connected to an electron donor, nutrients, and/or a vessel containing a donor and/or nutrients, other than the wastewater. The electron donor may be, for example, ethanol. The nutrients may be, for example, a chemically defined medium. The method may not include introducing another electron donor, nutrients, and/or fluid containing a donor and nutrients, other than the wastewater.

According to the method of reducing nitrogen oxide concentration in a sample according to an aspect, nitrogen oxide concentration in a sample may be effectively reduced.

A plug flow reactor for use in reducing nitrogen oxide concentration in a sample according to another aspect may be used to reduce nitrogen oxide concentration in a sample.

BRIEF DESCRIPTION OF THE DRAWINGS

The above and other aspects, features, and advantages of certain exemplary embodiments of the disclosure will be more apparent from the following detailed description taken in conjunction with the accompanying drawings, in which.

DETAILED DESCRIPTION

Figure 1:
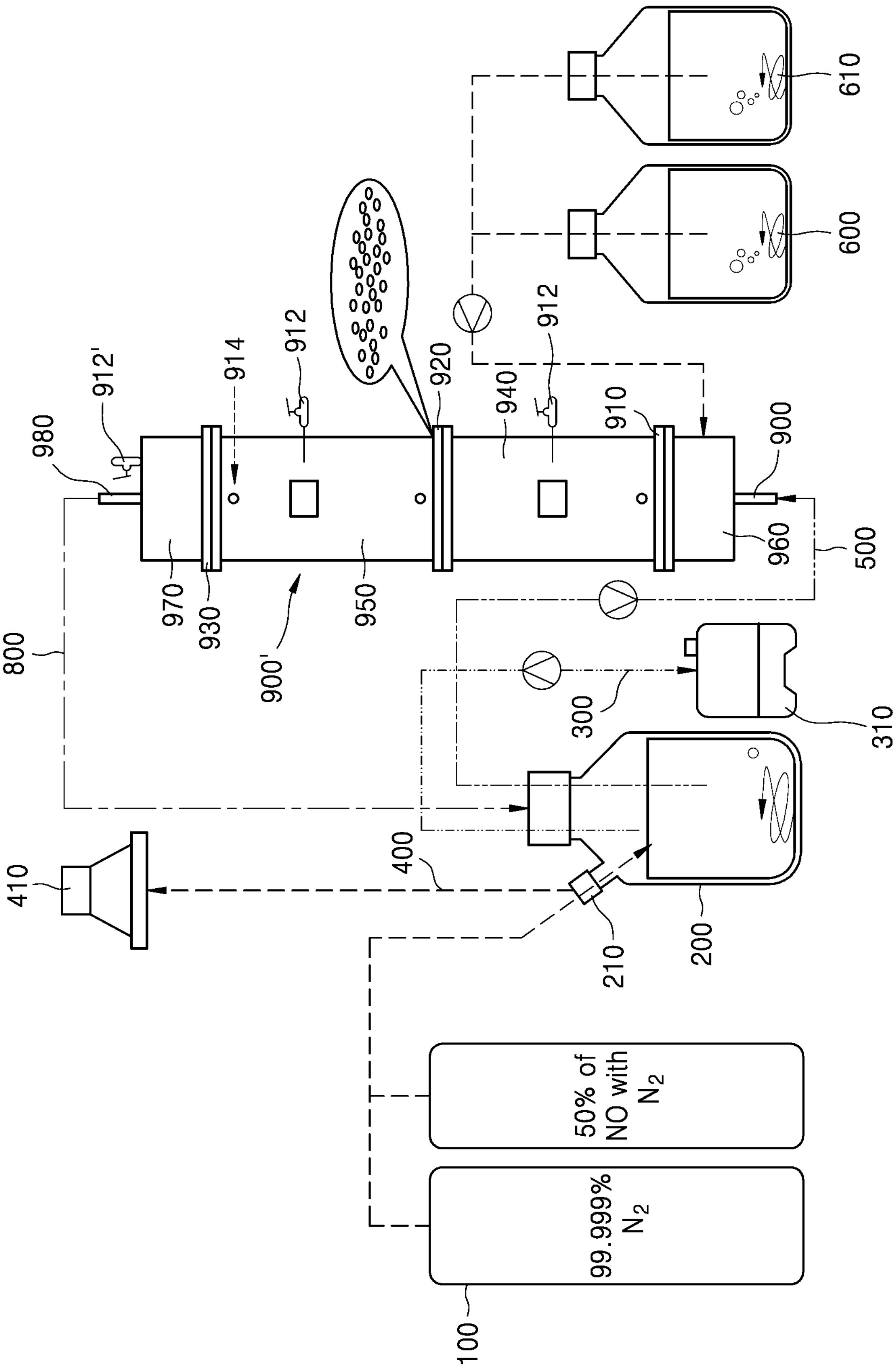
FIG. 1 is a diagram showing an example of a plug flow reactor system according to one or more embodiments.

Reference will now be made in further detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described in further detail below, and by referring to the figures, to explain certain aspects of the present detailed description. As used herein, the term "and/or" includes any and all combinations of at least one of the associated listed items. Expressions such as "at least one of," when preceding a list of elements, modify the entire list of elements and do not modify the individual elements of the list.

The terminology used herein is for the purpose of describing one or more exemplary embodiments only and is not intended to be limiting. As used herein, the singular forms "a," "an," and "the" are intended to include the plural forms as well, unless the context clearly indicates otherwise. The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

It will be understood that when an element is referred to as being "on" another element, it can be directly in contact with the other element or intervening elements may be present therebetween. In contrast, when an element is referred to as being "directly on" another element, there are no intervening elements present.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

The term "increase in expression", as used herein, refers to a detectable increase in the expression of a given gene. The "increase in expression" means that a gene expression level in a genetically modified (e.g., genetically engineered) cell is greater than the expression level of a comparative cell of the same type that does not have a given genetic modification (e.g., original or "wild-type" cell). For example, a gene expression level of a genetically modified cell may be increased by about 5% or greater, about 10% or greater, about 15% or greater, about 20% or greater, about 30% or greater, about 50% or greater, about 60% or greater, about 70% or greater, or about 100% or greater than an expression level of a non-engineered cell of the same type, i.e., a wild-type cell or a parent cell. A cell having an increased expression of a protein or an enzyme may be identified by using any method known in the art.

The term "copy number increase" may be caused by introduction or amplification of a gene in a cell, and encompasses a cell which has been genetically modified to include a gene that does not naturally exist in a non-engineered cell. The introduction of the gene may be mediated by a vehicle such as a vector. The introduction of the gene may be a transient introduction in which the gene is not integrated into a genome of the cell, or an introduction that results in integration of the gene into the genome of the cell. The introduction may be performed, for example, by introducing a vector into the cell, the vector including a polynucleotide encoding a target polypeptide, and then, replicating the vector in the cell, or integrating the polynucleotide into the genome of the cell. The term "copy number increase" may be an increase the copy number of a gene or genes encoding one or more polypeptides constituting a complex, and which together, exhibit nitrous oxide reductase activity.

The introduction of the gene may be performed via a known method, such as transformation, transfection, or electroporation. The gene may be introduced with or without the use of a vehicle. The term "vehicle", as used herein, refers to a nucleic acid molecule that is able to deliver other nucleic acids linked thereto, to a cell. In view of a nucleic acid sequence mediating introduction of a specific gene, the term "vehicle" may be used interchangeably with a vector, a nucleic acid construct, or a cassette. The vector may include, for example, a plasmid vector, a virus-derived vector, but is not limited thereto. The plasmid includes a circular double-stranded DNA sequence to which additional DNA encoding a gene of interest, may be linked. The vector may include, for example, a plasmid expression vector (e.g., a bacterial plasmid), a virus expression vector, such as a replication-defective retrovirus, an adenovirus, an adeno-associated virus, or a combination thereof. In an aspect, the vector may be a bacterial plasmid including a bacterial origin of replication and selectable marker.

The genetic modification disclosed herein may be performed by any suitable molecular biological method known.

The term "genetic modification", as used herein, refers to an artificial alteration in a constitution or structure of a genetic material of a cell.

Hereinafter, the exemplary embodiments will be described in more detail through examples. However, these examples are intended to illustrate the presented exemplary embodiments, and the scope of the present disclosure is not limited to these examples.

Example 1: Removal of Nitrogen Oxide in Sample by Using Plug Flow Reactor and Mixed Microbial Collection In the present example, nitrogen oxide included in a sample was reduced and removed by using a plug flow reactor as shown in FIG. 1. FIG. 1 is a diagram showing an example of a plug flow reactor system. The plug flow reactor system is as described hereinabove.

The plug flow reactor includes reaction compartments 940 and 950, each of which was a cylinder having a diameter of about 5 cm and a height of about 25 cm, with a total diameter:height ratio of about 1:10, and cylindrical buffer compartments 950 and 970, each of which with a diameter of about 5 cm and a height of about 10 cm. The reaction compartments 940 and 950 each had an internal reaction space of about 0.5 liters (L). The buffer compartments 960 and 970 each had an internal reaction space of about 0.2 L.

Each of the two compartments were filled with a plurality of disc-shaped carriers made of high-density polyethylene (HDPE) with an average diameter of about 0.8 cm. The disc-shaped carriers had a structure in which five plates are radially extended from a point near the center of the disk to form five pores.

At least some of microorganisms in the compartments were attached to the carriers to form biofilms. A process of forming a biofilm by attaching microorganisms to a carrier and growing the same was carried out by allowing activated sludge to adhere to the carriers by introducing sewage containing activated sludge derived from a sewage treatment facility at a flow rate of about 5 milliliters per minute (mL/min) while stirring through the upper outlet 980 of the plug flow reactor 900', and circulating at 25° C. for 24 hours. After removing the sewage through the inlet into the reactor 900' at a flow rate of about 5 mL/min to replace the sewage excluding the activated sludge with artificial sewage containing nutrients and Fe(III)(EDTA), artificial sewage was introduced at a flow rate of about 5 mL/min at 25° C. for 72 hours to form a biofilm by connecting the vessel 200 generating Fe(II)(EDTA)-NO, which is needed for the recirculation process, to the reactor outlet 980 and the inlet 900.

After inducing biofilm formation, it was confirmed that most of Fe(III) was reduced to Fe(II) by measuring the concentration of Fe(III) in the reactor 900'. That is, most of the introduced Fe(III)(EDTA) was reduced by the iron reducing microorganisms to exist in the form of Fe(II)$(EDTA)^2$.

After that, the pre-connected Fe(II)(EDTA)-NO generating vessel 200 was adjusted to hold 500 mL of an aqueous solution including Fe(II)$(EDTA)^{2-}$, and a gas, in which 99.999 vol % $N_2$ gas and NO (50 vol % in $N_2$) were mixed at a ratio of 100:1, was continuously purged in the vessel 200 at a flow rate of about 500 mL/min to contact with Fe(II)$(EDTA)^{2-}$ to form Fe(II)(EDTA)-NO, and then, the Fe(II)(EDTA)-NO-containing solution was introduced into the reactor 900' from the vessel 200 through the inlet 900. In this case, NO concentration in the incoming mixed gas was about 3,000 parts per million by volume (ppmv) to about 10,000 ppmv, which was three times or more greater than about 100 ppmv to about 1,000 ppmv, which was a NO concentration range in an exhaust gas actually discharged from a power plant. This Fe(II)(EDTA)-NO containing solution was used as an experimental group of the nitrogen oxide containing solution. In this regard, the formation process of Fe(II)(EDTA)-NO from nitrogen oxide seemed to be according to the following Reaction Scheme 1, but should not limited thereto:

$$[Fe(II)(EDTA)]^{2-} + NO_2(aq) <-> [Fe(II)(EDTA) - NO]^{2-}$$ Reaction Scheme 1

As a result, concentration of the produced $[Fe(II)(EDTA)\text{-}NO]^{2-}$ (which is used interchangeably with 'Fe(II)(EDTA)-NO' for convenience herein) was about 3.0 millimolar (mM).

Next, a solution containing about 1.0 mM of $[Fe(II)(EDTA)\text{-}NO]^{2-}$ in the Fe(II)(EDTA)-NO generating vessel 200 was introduced through the inlet 900 of the plug flow reactor. In this regard, flow rates were about 0.9 L/h and about 0.53 L/h, and hydraulic retention times (HRTs) of the fluid in each compartment were 1.06 hours and 0.53 hours, respectively. The HRT was calculated by Equation 1:

$$HRT = \text{reactor volume/flow rate} \quad \text{Equation 1}$$

In addition, in order to supply organic matter to microorganisms during the process, artificial wastewater was intermittently introduced from an artificial wastewater-containing vessel 600 into the buffer section 960 of the plug flow reactor. The artificial wastewater was artificial sewage made to simulate organic carbon and organic nitrogen and other components of sewage in sewage.

In addition, in order to supplement Fe(II)(EDTA) lost during the process, an aqueous solution containing 5 mM of Fe(III)(EDTA) was intermittently introduced at the same flow rate as the artificial wastewater from the Fe(III)(EDTA)-containing vessel 610 to the buffer compartment 960 of the plug flow reactor. As a result, the aqueous solution containing 5 mM of Fe(III)(EDTA) was two-fold diluted with the wastewater to obtain an aqueous solution containing 2.5 mM of Fe(III)(EDTA).

During the process operation, the Fe(II)(EDTA)-NO concentration in the solution flowing into the reactor and the Fe(II)(EDTA)-NO concentration in the solution flowing out from the reactor were measured. The Fe(II)(EDTA)-NO concentration in the solution flowing into the reactor and the Fe(II)(EDTA)-NO concentration in the solution flowing out from the reactor were measured by taking samples in the reaction compartments 940 and 950 from sampling ports 912 and 912', respectively.

The concentration of the Fe(II)(EDTA)-NO in the solution was measured by measuring absorbance at a wavelength of 425 nm by using a spectrophotometer. The NO concentrations at the inlet 210 and the outlet 500 of the Fe(II)(EDTA)-NO generating vessel 200 were measured by using a gas chromatograph-mass spectrometer. The concentrations of Fe(II) and total Fe were measured by using a spectrophotometer at a wavelength of 562 nm by using the Ferrozine assay. In this regard, [Total Fe—Fe(II)] concentration is Fe(III) concentration.

In addition, $N_2O$ concentration in the collected sample was measured. $N_2O$ concentration in the sample was measured by sampling 10 mL of the reactor solution by filtering through a 0.22 micron filter in a 27 mL vial filled with $N_2$, then stirring the sample for 15 minutes in order that the dissolved $N_2O$ is equilibrated with the headspace, and then by using an HP6890 Series gas chromatograph equipped with an HPPLOT/Q column.

In addition, the oxygen concentration in the reactor was measured during the process operation. The oxygen concentration was measured by attaching sensor spots to the inlet 900 of the reactor, at the bottom of the lower compartment 940, and on top of the upper compartment 950, rather than by measuring oxygen concentration in the solution, and by using a non-contact method using the principle that a fiber-optic oxygen sensor of a FireSting$O_2$ device emits near-infrared (NIR) light in response to oxygen. That is, oxygen was measured by using sensor spots inside the reactor and an optical fiber sensor outside the reactor.

Oxygen concentration of the solution flowing into the reactor and the oxygen concentration of the solution flowing out from the reactor were measured by using oxygen dots 914 in the reaction compartments 940 and 950, respectively. The oxygen dots 914 are sensor spots, which are capable of measuring oxygen concentration in the solution. Oxygen concentration was measured by using a FireSting$O_2$—Optical Oxygen Meter.

Table 1 shows results of measuring Fe(II)(EDTA)-NO concentration in the solution flowing into the reactor and Fe(II)(EDTA)-NO concentration in the solution flowing out from the reactor. In Table 1, in the process with operating times of 24 hours and 72 hours (hereinafter "Process Operation 1"), the sample inflow flow rate was about 0.9 L/h, the hydraulic retention time (HRT) of the fluid in each compartment was 1.06 hours, and the process with operating times of 168 hours and 192 hours (hereinafter "Process Operation 2") had a sample inflow flow rate of about 1.8 L/h and hydraulic retention time (HRT) of the fluid in each compartment of 0.53 hours. That is, Process Operation 2 had twice the flow rate, while HRT was 0.5 times shorter, compared to Process Operation 1.

TABLE 1

| Operation time (hours) | Inflow concentration (mM) | Outflow concentration (mM) | NO removal efficiency (%) |
|---|---|---|---|
| 24 | 2.51 | 0.86 | 65.7 |
| 72 | 0.99 | 0.24 | 75.8 |
| 168 | 1.35 | 0.16 | 88.1 |
| 192 | 1.30 | 0.18 | 86.2 |

Figure 2:
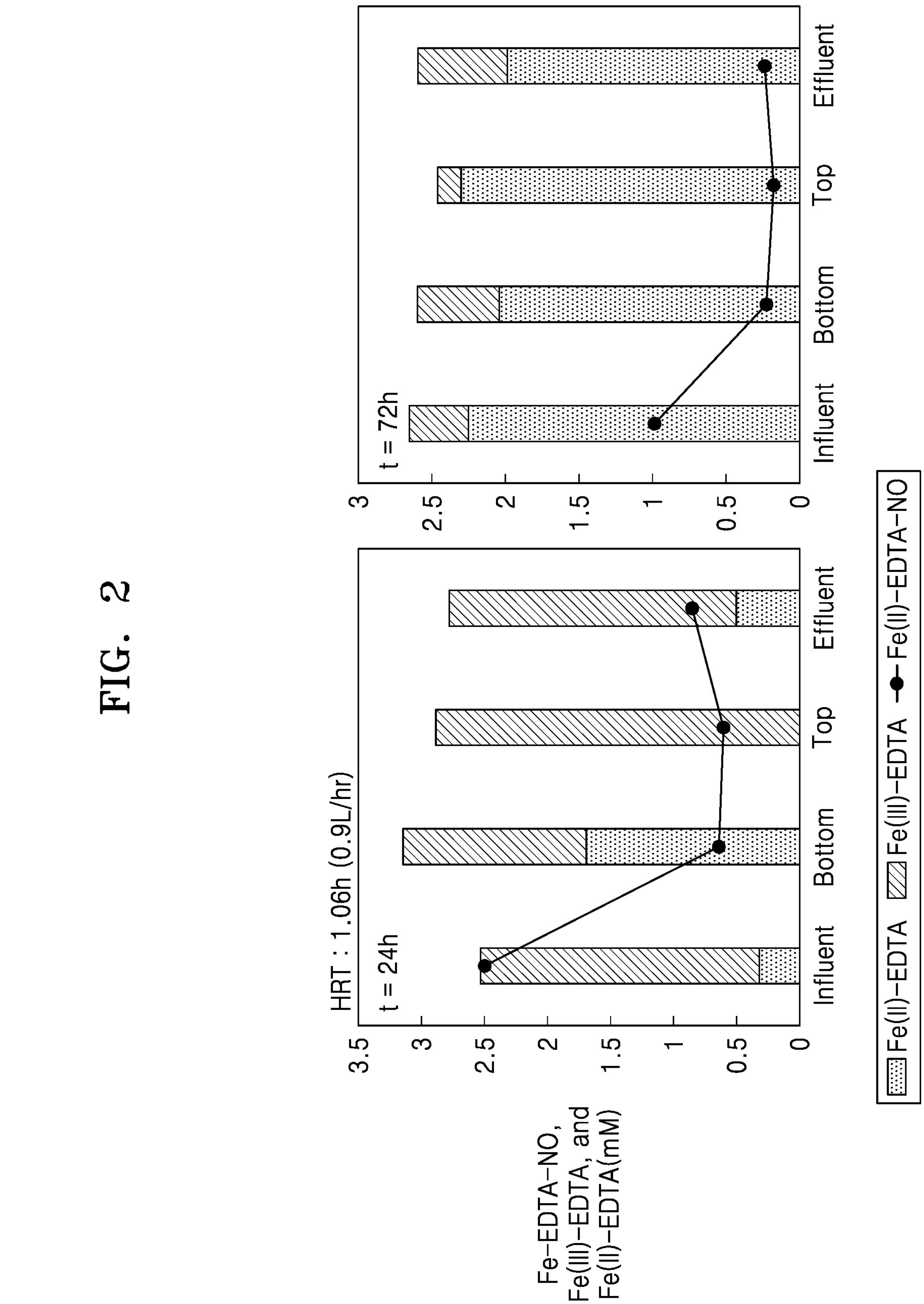
FIG. 2 shows concentrations of Fe(II)(EDTA), Fe(III)(EDTA), and Fe(II)(EDTA)-NO at an inlet, a lower compartment, an upper compartment, and an outlet, when operated at a flow rate of 0.9 liters per hour (L/h) and a hydraulic retention time (HRT) of 1.06 hours.

As shown in Table 1, in the case of Process Operation 1, up to 75.8% of NO removal efficiency could be achieved. In addition, in the case of Process Operation 2, up to 88.1% of NO removal efficiency could be achieved. In addition, even when a sample containing about 3,000 ppmv to about 10,000 ppmv of high concentration NO was introduced into the plug flow reactor, the growth of microorganisms and the denitrification and iron reduction reactions were smoothly performed. FIG. 2 shows concentrations of Fe(II)(EDTA), Fe(III)(EDTA), and Fe(II)(EDTA)-NO at the inlet, lower compartment, upper compartment, and outlet, when operated at a flow rate of 0.9 L/h and HRT of 1.06 hours. In FIGS. 2, A and B were operated with operation times of 24 hours and 72 hours, respectively.

Figure 3:
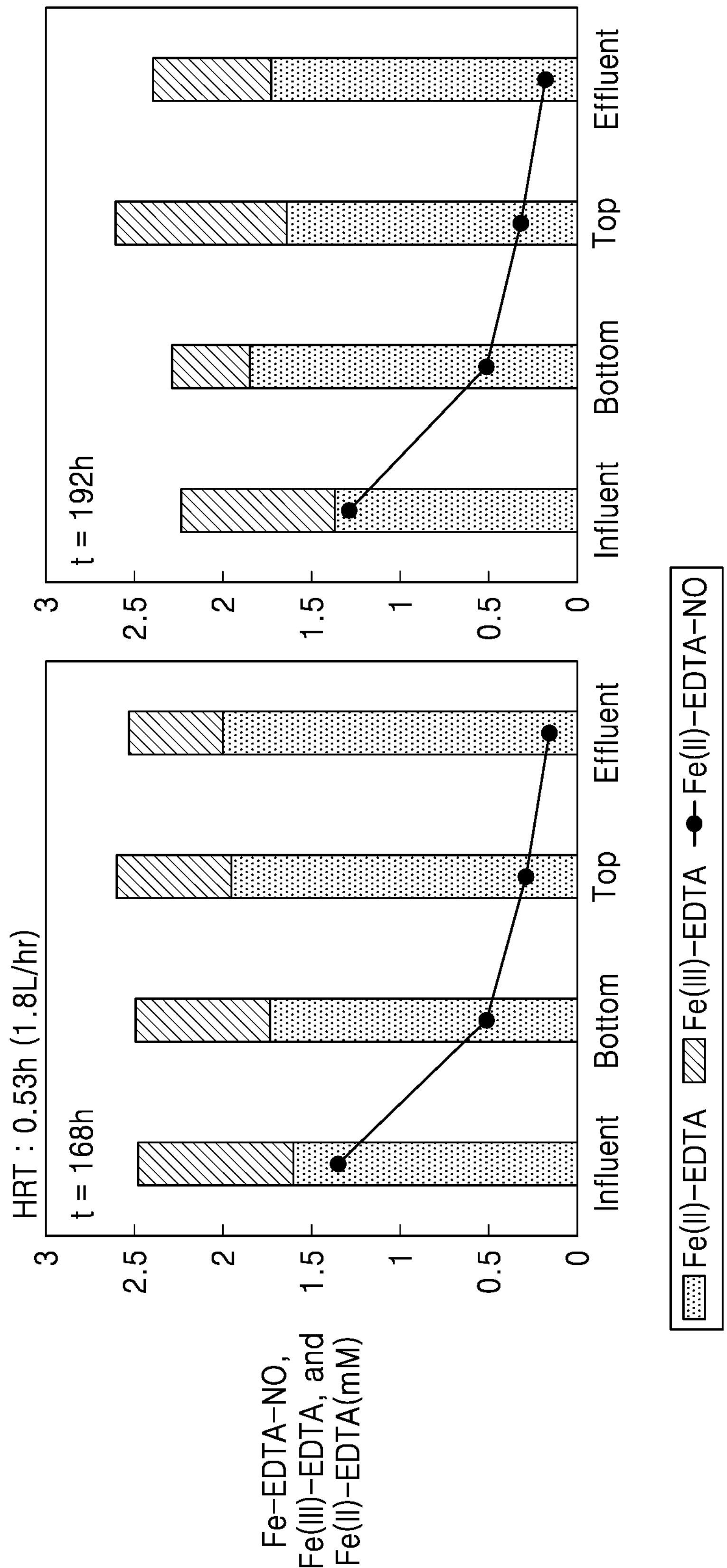
FIG. 3 shows concentrations of Fe(II)(EDTA), Fe(III)(EDTA), and Fe(II)(EDTA)-NO at an inlet, a lower compartment, an upper compartment, and an outlet, when operated at a flow rate of 1.8 L/h and HRT of 0.53 hours.

FIG. 3 shows concentrations of Fe(II)(EDTA), Fe(III)(EDTA), and Fe(II)(EDTA)-NO at the inlet, lower compartment, upper compartment, and outlet, when operated at a flow rate of 1.8 L/h and HRT of 0.53 hours. In FIGS. 3, A and B were operated with operating times of 168 hours and 192 hours, respectively.

In addition, as a result of measuring oxygen concentrations in the reactor solution, oxygen concentration in the buffer compartment 960 was 0.9±0.2%, in the lower section 940 was 0.4±0.1%, and in the upper section 950 was 0%.

In addition, as a result of measuring $N_2O$ concentration in the reactor solution, in the case of Process Operation 1, $N_2O$ concentration discharged through the outlet was 0.9 micromoles per hour (μmole/h), and in the case of Process Operation 2, $N_2O$ concentration discharged through the outlet was 3.6 μmole/h. Therefore, when NO in a more realistic NO concentration range of about 100 ppmv to about 1,000 ppmv is introduced into the reactor, the $N_2O$ concentration discharged through the outlet is expected to be lowered to a value close to zero.

Example 2: Removal of Nitrogen Oxide in Sample by Using Plug Flow Reactor and Recombinant *E. coli*

In the present example, nitrogen oxide contained in a sample was reduced and removed by using a plug flow reactor as shown in FIG. 1, except for using the medium containing vessel 600 instead of the artificial wastewater containing vessel 600, without going through a recirculation process. In this regard, the microorganisms used for the biological reaction were recombinant *E. coli* (DE3) in which a NosZ gene, which encodes a nitrous oxide ($N_2O$) reductase, was inserted. The recombinant *E. coli* (DE3) is disclosed in US Patent Publication No. US2022/0177896A1, the content of which are incorporated herein in their entirety.

The plug flow reactor included two reaction compartments 940 and 950, each of which is a cylinder having a diameter of 5 cm and a height of 25 cm, with a diameter: height ratio of 1:5, and cylindrical buffer compartments 960 and 970, each of which with a diameter of 5 cm and a height of 10 cm. The reaction compartments 940 and 950 each have an internal reaction space of 0.5 L. The buffer compartments 960 and 970 each have an internal reaction space of 0.2 L.

Each of the two compartments was filled with a plurality of disk-shaped carriers made of high-density polyethylene (HDPE) with a diameter of about 0.8 cm. The disk-shaped carriers have a structure in which five plates are radially extended from a point near the center of the disk to form five pores.

At least some of the microorganisms in the compartments were attached to the carriers to form biofilms. The process of forming a biofilm by attaching microorganisms to a carrier and growing the same was by inoculating the recombinant *E. coli* (DE3) into nutrient-rich yeast extract tryptone (YT) medium (tryptone 16 g/L, yeast extract 10 g/L, NaCl 5 g/L, and $CuCl_2$ 67.2 mg/L), culturing the same at 35° C. under aerobic conditions for 24 hours, introducing the obtained culture through the inlet of the plug flow reactor at a flow rate of 5 mL/min, and supplying 2 g/L of glucose at a flow rate of 0.3 L/h at 25° C. for 72 hours to form a biofilm.

First, a 6 mM solution of Fe(II)(EDTA)-NO was added to water prepared externally in the Fe(II)(EDTA)-NO-containing vessel 200, and a solution containing about 6.0 mM Fe(II)(EDTA)-NO was introduced through the inlet 900 of the plug flow reactor from the container 200, at a flow rate of 0.21 L/h. In this regard, hydraulic retention time (HRT) of the fluid in each compartment was 2.0 hours.

In addition, medium was continuously introduced into the buffer compartment 960 of the plug flow reactor from the medium-containing vessel 600 at a flow rate of 0.21 L/h, in order to supply organic matter to the microorganisms during the process. The medium is 2× M9 medium containing 2 g/L glucose. M9 medium includes 6.78 g/L of $Na_2HPO_4$, 3 g/L of $KH_2PO_4$, 0.5 g/L of NaCl, 1 g/L of $NH_4Cl$, 0.2 g/L of $MgCl_2$ $6H_2O$, and 1 mL of 1000× trace metal (0.5 g/L of $MnSO_4$, 0.1 g/L of $Na_2MoO_4$, 0.1 g/L of $CuSO_4$ $5H_2O$, and 2 g/L of $CaCl_2$)).

During the process operation, the Fe(II)(EDTA)-NO concentration in the solution flowing into the reactor and the Fe(II)(EDTA)-NO concentration in the solution flowing out from the reactor were measured. The Fe(II)(EDTA)-NO concentration in the solution flowing into the reactor and the Fe(II)(EDTA)-NO concentration in the solution flowing out from the reactor were measured by taking samples in the reaction compartments 940 and 950 from sampling ports 912 and 912', respectively.

The concentration of the Fe(II)(EDTA)-NO in the solution was measured by measuring absorbance at a wavelength of 425 nm by using a spectrophotometer. The NO concentrations at the inlet 210 and the outlet 500 of the Fe(II)(EDTA)-NO generating vessel 200 were measured by using a gas chromatograph-mass spectrometer. The concentrations of Fe(II) and total Fe were measured by using a spectrophotometer at a wavelength of 562 nm by using the Ferrozine assay. In this regard, [Total Fe—Fe(II)] concentration is Fe(III) concentration.

In addition, $N_2O$ concentration in the collected sample was measured. $N_2O$ concentration in the sample was measured by sampling 10 mL of the reactor solution by filtering through a 0.22 μm filter in a 27 mL vial filled with $N_2$, then stirring the sample for 15 minutes in order that the dissolved $N_2O$ was equilibrated with the headspace, and then by using an HP6890 Series gas chromatograph equipped with an HPPLOT/Q column.

In addition, oxygen concentration in the reactor was measured during the process operation. The oxygen concentration was measured by attaching sensor spots to the inlet 900 of the reactor, the bottom of the lower compartment 940, and the top of the upper compartment 950, rather than by measuring oxygen concentration in the solution, and by using a non-contact method using the principle that a fiber-optic oxygen sensor of a FireSting$O_2$ device emits near-infrared (NIR) light in response to oxygen. That is, oxygen was measured by using sensor spots inside the reactor and an optical fiber sensor outside the reactor.

Oxygen concentration of the solution flowing into the reactor and the oxygen concentration of the solution flowing out from the reactor were measured by using oxygen dots 914 in the reaction compartments 940 and 950, respectively. The oxygen dots 914 are sensor spots, which are capable of measuring oxygen concentration in the solution. Oxygen concentration was measured by using a FireSting$O_2$—Optical Oxygen Meter.

Table 2 shows results of measuring the maximum concentration of $N_2O$ generated and measured in the central portion of the upper compartment 950 of the reactor, $N_2O$ concentration in the solution flowing out through the outlet, and $N_2O$ removal efficiency. Table 3 shows the NO removal efficiency as a result of the process.

TABLE 2

| Operation time (hours) | Maximum concentration of generated $N_2O$ (μM) | Outflowing $N_2O$ concentration (μM) | $N_2O$ removal efficiency (%) |
|---|---|---|---|
| 72 | 96 | 90 | 6.3 |
| 96 | 131 | 121 | 7.8 |

TABLE 3

| Operation time (hours) | Inflowing Fe-EDTA-NO concentration (mM) | Outflowing Fe-EDTA-NO concentration (mM) | NO removal efficiency (%) |
|---|---|---|---|
| 72 | 1.02 | 0.69 | 32.3 |
| 96 | 0.53 | 0.23 | 56.6 |

Figure 4:
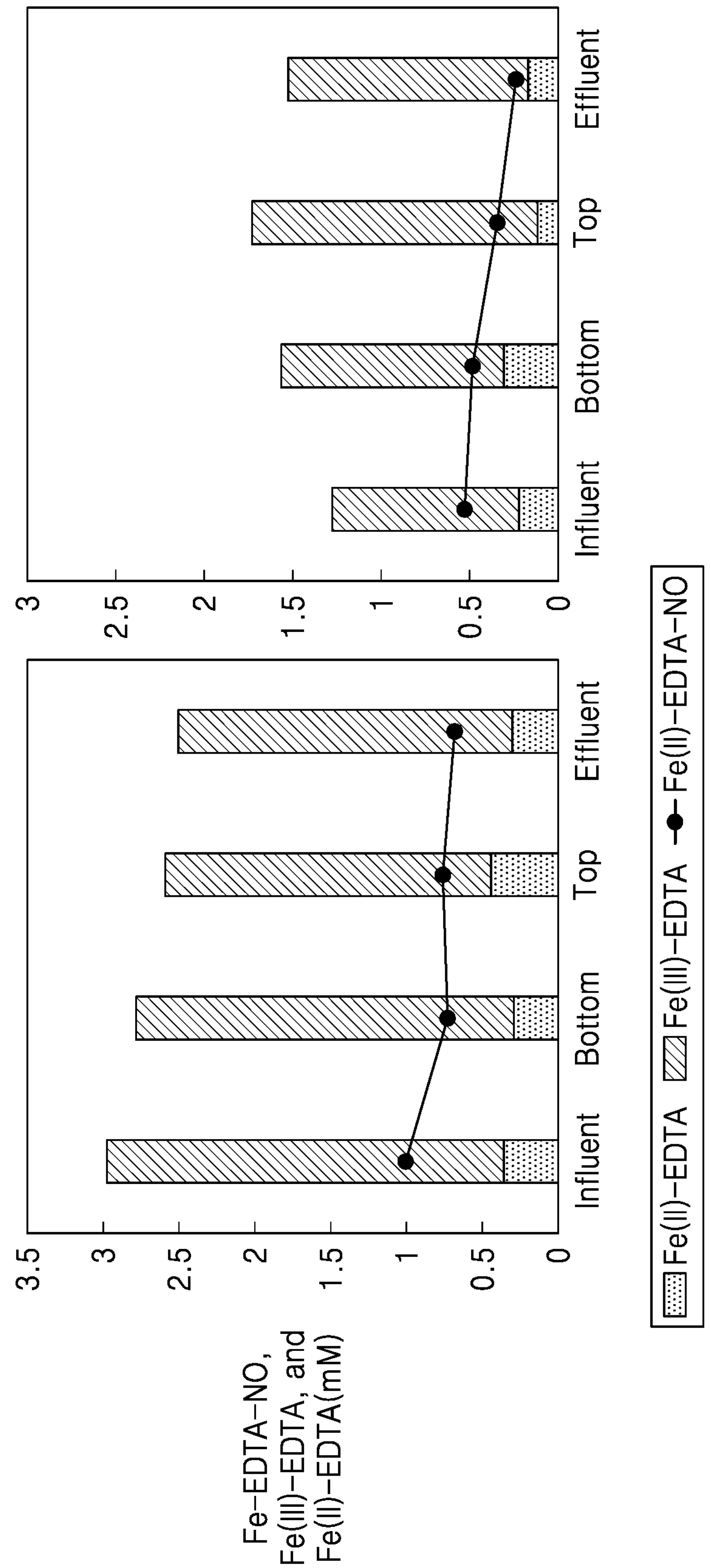
FIG. 4 shows concentrations of Fe(II)(EDTA), Fe(III)(EDTA), and Fe(II)(EDTA)-NO at an inlet, a lower compartment, an upper compartment, and an outlet, when operated at a flow rate of 0.5 L/h and HRT 2.0 hours.

As shown in Tables 2 and 3, even when recombinant *E. coli* with enhanced denitrification ability were used as microorganisms of a single kind, and a chemically defined medium was used as the medium, the NO in the fluid could be removed. FIG. 4 is a diagram showing concentrations of Fe(II)(EDTA), Fe(III)(EDTA), and Fe(II)(EDTA)-NO at the inlet 900, the lower compartment 940, the upper compartment 950, and the outlet 980, when operated at a flow rate of 0.5 L/h and HRT of 2.0 hours. In FIGS. 4, A and B were operated with operation times of 72 hours and 96 hours, respectively.

In addition, as a result of measuring oxygen concentrations in the bioreactor solution, all were 0%.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. While one or more exemplary embodiments have been described with reference to the figures, it will be understood by those of ordinary skill in the art that various changes in form and details may be made therein without departing from the spirit and scope of the disclosure as defined by the following claims.

What is claimed is:

1. A method of reducing a concentration of a nitrogen oxide, the method comprising:

contacting a microorganism with a nitrogen oxide-containing sample to reduce the concentration of the nitrogen oxide in the sample, wherein the contacting comprises contacting the microorganism with Fe(II)(L)-$NO_x$ in a bioreactor, wherein the bioreactor is a plug flow reactor comprising a plurality of carriers, wherein the Fe(II)(L)-$NO_x$ is a complex in which a chelating agent, $Fe^{2+}$, and $NO_x$ are chelated, wherein L is the chelating agent, and wherein $NO_x$ is a nitrogen oxide ligand.

2. The method of claim 1, wherein L is ethylenediamine, diethylenetriamine, triethylenetetraamine, hexamethylenetetramine, N-(2-hydroxyethyl)ethylenediaminetriacetic acid, ethylenediaminetetraacetic acid, iminodiacetic acid, nitrilotriacetic acid, diethylenetriaminepentaacetic acid, or a combination thereof.

3. The method of claim 1, wherein the microorganism is a single microorganism or a combination of different microorganisms.

4. The method of claim 3, wherein the single microorganism comprises a recombinant microorganism of the genus *Escherichia*, and the combination of different microorganisms is a microbial collection derived from activated sludge or sewage.

5. The method of claim 4, wherein the recombinant microorganism of the genus *Escherichia* comprises a genetic modification that increases expression of a nosZ gene encoding a nitrous oxide reductase NosZ in the recombinant microorganism, a nosR gene encoding NosR, a nosD gene encoding NosD, a nosF gene encoding NosF, a nosY gene encoding NosY, and an apbE gene encoding ApbE, wherein the nosZ gene, the nosR gene, the nosD gene, the nosF gene, the nosY gene, and the apbE gene are derived from a microorganism of the genus *Pseudomonas*, the genus *Paracoccus*, or a combination thereof.

6. The method of claim 1, wherein the plug flow reactor comprises two or more compartments, wherein each of the two or more compartments are separated from each other by a porous plate comprising a plurality of pores.

7. The method of claim 6, wherein the two or more compartments comprises:

a first compartment comprising a bacterium that reduces $NO_2$ and/or NO to $N_2$, and a second compartment comprising a bacterium that reduces Fe(III) to Fe(II).

8. The method of claim 7, wherein the sample flows within the bioreactor in the direction from the first compartment to the second compartment.

9. The method of claim 7, wherein the bacterium that reduces $NO_2$ and/or NO to $N_2$ is a microorganism of the family Rhodocyclaceae, Zoogloeaceae, Rhodobacteraceae, Clostridiaceae, or a combination thereof, and the bacterium that reduces Fe(III) to Fe(II) is a microorganism of the family Clostridiaceae, Shewanellaceae, Geobacteraceae, Rhodobacteraceae, Pseudomonadaceae, or a combination thereof.

10. The method of claim 1, wherein the contacting further comprises flowing the sample through the bioreactor.

11. The method of claim 1, wherein the Fe(II)(L)-$NO_x$ is Fe(II)(EDTA)-NO.

12. The method of claim 10, wherein the sample flowing out from the bioreactor is recirculated back into the bioreactor.

13. The method of claim 10, wherein the sample flowing out from the bioreactor is recirculated back into the bioreactor by recombining with the nitrogen oxide-containing sample.

14. The method of claim 1, wherein the bioreactor is fluidly connected to a wastewater-containing vessel or a Fe(III)(EDTA)-containing vessel.

15. The method of claim 1, further comprising introducing wastewater or Fe(III)(EDTA) into the bioreactor.

* * * * *